United States Patent [19]
Fournie

[11] Patent Number: 6,033,846
[45] Date of Patent: Mar. 7, 2000

[54] PROCESS FOR DOSING OF DEOXYRIBONUCLEIC ACID FOUND IN AN EXTRACELLULAR POSITION IN A MEDIUM

[75] Inventor: Gilbert J. Fournie, Toulouse, France

[73] Assignee: Societe Francaise de Recherches et d'Investissements Societe Anonyme, France

[21] Appl. No.: 07/744,348

[22] Filed: Aug. 13, 1991

[51] Int. Cl.[7] ............................. C12Q 1/68; C12P 19/34; G01N 33/00

[52] U.S. Cl. ............................. 435/6; 435/91.1; 436/94; 436/800

[58] Field of Search ..................... 435/6, 91.1; 536/23.1, 536/24.33, 25.3; 530/358; 935/77; 436/94, 800

[56] References Cited

U.S. PATENT DOCUMENTS

| | | | |
|---|---|---|---|
| 4,468,346 | 8/1984 | Paul et al. | 260/112 B |
| 4,556,643 | 12/1985 | Paau et al. | 436/501 |
| 4,617,261 | 10/1986 | Sheldon et al. | 435/6 |
| 4,767,699 | 8/1988 | Vary et al. | 435/6 |
| 4,840,893 | 6/1989 | Hill et al. | 435/6 |

OTHER PUBLICATIONS

Fournie, et al., *Analytical Biochemistry*, vol. 158, pp. 250–256, 1986.
Kung, et al., *Analytical Biochemistry*, vol. 187, pp. 220–227, 1990.
Bos, et al., *Journal of Immunoassay*, 2(3&4), 187–204, (1981).
G.J. Fournie et al. Anal. Biochem. 158, 250–256 (1986).
J. Briggs et al. Am. Clin. Lab. 8, 36–41 (1989).
R.D. Dyson Essentials of Cell Biology (2nd Edition), pp. 147–148, Allyn and Bacon, Inc., Boston (1978).
J. Meinkoth and G.M. Wahl Methods in Enzymology 152, 91–94 (1987).
D.M. Wallace Methods in Enzymology 152, 33–41 (1987).
P.R. Langer et al. Proc. Natl. Acad. Sci. USA 78, 6633–6637 (1981).
V.T. Kung et al. Anal. Biochem. 187, 220–227 (1990).
E.S. Bos et al. J. Immunoassay 2, 187–204 (1981).

*Primary Examiner*—Bradley L. Sisson
*Attorney, Agent, or Firm*—Roylance, Abrams, Berdo & Goodman, L.L.P.

[57] ABSTRACT

The present invention relates to a process for the dosage of Deoxyribonucleic Acid (DNA) present in an extracellular position in a medium.

The process consists in the following steps:
- fixation of DNA present in the medium on a support.
- incorporation of at least one label led deoxyribonucleotide into the fixed DNA.
- direct or indirect detection of the incorporated marker.

Application to all situations in which it is important to detect and/or dose DNA present in a medium in an extracellular position, such as for example:
- physiological or physiopathological situations in which it is important to quantify in vivo or in vitro the intensity of cell death phenomena,
- in pharmacotoxicology, in vivo or in vitro detection of the cytotoxicity of a toxic substance or drug,
- the study of the biocompatibility of biomaterials used, in particular, in extracorporeal circulation and haemodialysis systems,
- detection of DNA contaminating preparations of biologically active substances (particularly proteins or vaccins) obtained by genetic engineering techniques.

29 Claims, No Drawings

PROCESS FOR DOSING OF DEOXYRIBONUCLEIC ACID FOUND IN AN EXTRACELLULAR POSITION IN A MEDIUM

The present invention relates to a new process for dosing microquantities of deoxyribonucleic acid (DNA) found in an extracellular position in a liquid medium.

Such a dosage is of great relevance in a number of circumstances:

1. From a physiological point of view, the presence of DNA in an extracellular position in a living organism can depend on two kinds of phenomena. On the one hand, cell death is a normal and permanent phenomenon which leads to the release of products of chromatin degradation (and thus DNA) into the extracellular medium and whose role in phenomena relating to the development of the organism and the maturation of various functional systems (particularly the immune system) is now well-established. On the other hand, some authors have theorized that the release of DNA into the extracellular space might depend on an active cell process of excretion and could thus represent a mechanism of intercellular communication.

2. From a pathological point of view, all processes accompanied by phenomena relating to the destruction of a living structure containing DNA, be it the cells of a multicellular organism or infectious particles (bacterial, viral or parasitic), lead to the release of DNA (and/or RNA) into adjacent extracellular media. The importance of this phenomenon, the relevance of its study and the methodologies used to explore it are not univocal (Fournié, Eurorhumatology, Tagasand Son Press, Athens, 1987, pp 9–13).

A/ During the course of certain diseases, particularly infectious or hereditary diseases, DNA specific to a pathogenic agent or a pathogenic process may be present in the extracellular liquid. Detection and identification of this DNA can thus be of etiological interest. In these situations, hybridization techniques are most often used. The principle of these techniques is to bring together DNA potentially present in a sample to be tested (previously purified and denatured by heat and fixed on a solid support) and an additional DNA probe, previously labelled either with a radioactive substance or with a cold marker, for example biotin. Fixing DNA on a solid support is most often carried out on a membrane (nylon or nitrocellulose for example). This method is relatively long and is only semi-quantitative but allows specific DNA at the picogram level to be detected, even when using "cold" labelling of DNA (Barraud-Hadidane et al., Arch Toxicol, 1987, Suppl 11, 200–205). A quantitative technique using a microtitration plate as a solid support and a biotin-labelled DNA probe has also been described by Nagata et al. (FEBS, 1985, 183, 379–382).

B/ On the other hand, in many circumstances, it may be important to detect and dose DNA independently of its specificity, i.e. the molecular characteristics of its primary structure:

1/ In human pathology, dosage of DNA may be, depending on the circumstances, either of diagnostic and/or physiopathological relevance:

a/ Release of DNA into the extracellular space reflects and is evidence of the process of cell death and can allow this cell death to be detected and quantified in vivo throughout the whole organism. Detection and dosage of DNA can thus be of diagnostic and prognostic significance in many cases of experimental or human pathology. This is the case, for example, for thromboembolic disease (Vargo et al., Chest. 1990, 97, 63–68) and vasculitis (Steinman, Arthritis Rheum, 1982, 25, 1425–1430).

b/ It is possible that circulating DNA may play a pathogenic role. Different mechanisms may be involved: (i) due to its physicochemical properties, particularly its viscosity and electric charge, circulating DNA may disturb normal functioning of circulation and/or become preferentially deposited in certain tissues or organs; (ii) extracellular DNA may activate various biological systems, such as the complement and coagulation systems; (iii) it may also play a pathogenic role due to its "genic" nature and properties by becoming integrated into the host's genome; (iv) finally, it may be at the basis of the formation of macromolecular complexes in the presence of antibodies, a mechanism implicated in the development of glomerular lesions in patients suffering from disseminate lupus erythematosus (Fournié, Kidney Int, 1988, 33, 487–497).

2/ In Pharmacotoxicology, dosage of circulating DNA can help detect the cytotoxicity of a medicinal or toxic substance in vivo (Bret et al., Toxicology, 1990, 61, 283–292). It might thus be useful, during the drug-development phase, in the selection, within a same pharmacological class, of the the substance with the best efficacy/toxicity ratio. Moreover, it could be used during the course of phase I clinical trials in man for early detection of medicinal toxicity not predictable from experimental pharmaco-toxicological data. Finally, dosage of DNA found in extracellular positions in various biological liquids, particularly in the urine, may be useful for routine screening of the toxic effects of different xenobiotics and drugs.

3/ In the field of biocompatibility studies on various extracorporeal circulation systems used in medical practice, particularly hemodialysis systems, dosage of DNA allows in vivo analysis of the intensity of cell death phenomena related to possible bio-incompatibility of the system (Fournié et al., Amer J Nephrol, 1989, 9, 384–391).

4/ In the field of biotechnology, dosage of residual DNA contaminating media containing active biological substances obtained, for example, by genetic engineering is important in the control of innocuousness (WHO expert committee on biological standardization, 1982). Given the importance of dosing circulating DNA and DNA found in extracellular positions in various biological liquids, different calorimetric, fluorimetric, immunological and biological techniques have been developed. These concern, on the one hand, the specificity, sensitivity and quantitative nature of the dosage and, on the other hand, the necessity of carrying out preliminary treatment of the sample on which the dosage is to be carried out 1/ The specificity of certain techniques is not assured because of interaction between various substances other than DNA present in the sample to be dosed and the reagents used in the dosage method. This is true for fluorimetric and calorimetric techniques, as well as for immunological techniques and methods using DNA-fixing substances. Control of the specificity of dosage systematically requires additional dosage to be carried out after digestion of dosed DNA, using a specific enzyme such as deoxyribonuclease I (Steinman, J Clin Invest, 1975, 56, 512–515).

2/ Limitations in sensitivity and the absence of a quantitative nature of the techniques are related to various factors: (i) the actual principle of some techniques (e.g. counter-immunoelectrophoresis) does not allow quantitative dosage to be carried out in some cases; (ii) the variable size of DNA molecules to be dosed: the number of DNA molecules with different sizes is variable even for a same quantity, whereas the signal detected is a function of the number of reactive DNA molecules (and not of the absolute amount of DNA as expressed by the number of nucleotides or base pairs); (iii) DNA losses linked to low yields when the quantities of DNA to be purified are small.

3/ Treatment of the sample before dosage, to purify and concentrate DNA as required by some techniques, is often laborious and sometimes random, leading to limitations, as mentioned earlier, in the quantitative recovery of DNA present in the original sample unless methods are used that are difficult to set up in practice, such as ultracentrifugation (Shapiro, Anal Biochem, 1981, 110, 229–231).

In order to overcome these limitations and difficulties, new methods for the recovery and purification of DNA, as well as the use of the methods and materials used in molecular biology, have been suggested for the quantitative dosage of DNA.

1/ Raptis and Ménard (J Clin Invest, 1980, 66, 1391–1399) were the first to detect circulating DNA in patients with disseminate lupus erythematosus, after having purified and labelled it in vitro with a radioactive isotope using a haplotomic cut displacement technique ("Nick translation"), previously described by Rigby et al. (J Moi Biol, 1977, 113, 237–251). The laboriousness of techniques for the preparation of the material to be dosed (dilution of the sample, enzymatic digestion, organic extraction, dialysis, column purification, precipitation with ethanol) prohibits the application of this method to routine detection and dosage of DNA.

2/ Fournié et al. (Anal Biochem, 1986, 158, 250–256) have described a new process for the recovery and dosage of microquantities of DNA in an acellular biological liquid. This method, based on extraction of DNA by treatment with phenol, its recovery by precipitation with ethanol using gelatin as a co-precipitating agent and quantitative dosage using haplotomic cut displacement techniques, has resolved the problem of simultaneous treatment of several samples compatible with the use of this method in some routine applications. The limitations of this method are: (i) the necessity of extracting the sample before dosing it, which requires several centrifugation steps at different temperatures, a lyophilization or evaporation under vacuum step and a step for redissolution of the sample; (ii) the need for radioactive labelling of DNA; (iii) the steps concerning washing the filters on which samples for the preparation of DNA radiolabelled with a tritium-labelled free nucleotide have been deposited (steps which cannot be easily used in the case of labelling DNA with biotin or any other "cold" marker due to the difficulty in eluting DNA adsorbed onto the filter).

3/ Briggs et al. (American Biotechnology Laboratory, June 1989, pp 18–25) have described a "total DNA assay system" which allows enzymatic dosage of DNA at the picogram level (2–200 pg). According to this method, purified and heat-denatured DNA is fixed on a membrane through the intermediate of a protein for fixing single-stranded DNA and is quantified using an anti-single stranded DNA monoclonal antibody coupled to an enzyme (urease), using a potentiometric biosensor developed by Molecular Devices Corp (Menlo Park, Calif., USA). This method has a number of limitations, in particular: (i) the use of a special and costly apparatus (>200 000 FF) for carrying out the dosage; (ii) the non-quantitative nature of the dosage, "yield" being a function of the size of DNA molecules; (iii) the necessity of pretreatment "adapted" to each type of sample (denaturation of DNA with heat, prefiltration on nitrocellulose and digestion with proteinase K, possibly followed by separation, depending on the size of DNA).

The latter two techniques can be used for small volumes and allow extracellular DNA to be dosed independently of its nature at the picogram level, but they cannot be used within the context of the aims of the present invention, that is, dosage of quantities of DNA on the order of several picograms in complex biological liquids (i) not requiring preliminary extraction of DNA before dosage, (ii) not requiring the use of radioactive isotopes, (iii) that can be carried out on a solid support, in particular on a microtitration plate, (iv) allowing results to be obtained in less than two hours.

The aim of the present invention is to provide a DNA-dosage process which is better adapted to routine requirements than processes of the prior art. In fact, the new process of the present invention:

can be carried out on a conventional "microtitration plate" type solid support on which the various reactions required for dosage are carried out, does not require extraction of DNA before the actual dosage steps, particulary when the samples are blood plasma samples, does not require the use of radioactive substances, does not require a specific apparatus as the signal can be read on a conventional spectrophotometer, spectrofluorimeter or biosensor, requires only a few microliters of sample, is specific to DNA, is extremely sensitive, can be used simultaneously on more than a hundred samples, and allows the result of the dosage to be obtained in less than two hours.

The subject of the present invention is a process for dosage of microquantities of DNA present in extracellular positions in a biological liquid, particularly blood plasma, wherein it includes the following steps:

adsorption of DNA to be dosed onto a solid support, labelling this DNA by incorporation of one or more labelled deoxyribonulceotide triphosphates involving an enzyme or enzymes specific to DNA, dosage of DNA by an appropriate method to detect the marker incorporated into the DNA. These steps can be separated from one another by washing steps.

According to a preferred mode of an embodiment of the process of with the present invention, adsorption of DNA onto a solid support is carried out through the intermediate of substances consisting of gelatin or cationic macromolecular complexes with a strong affinity for DNA.

According to an advantageous modality of this mode of embodiment, the substances used to adsorb DNA consist of a historic protein or historic proteins. According to an advantageous disposition of this mode of embodiment, the solid support is sensitized by incubation of a mixture of historic proteins in 0.05–0.1M carbonate buffer (pH about 9.6) for several hours, whatever the incubation temperature.

According to a preferred embodiment of the process conforming with the present invention, adsorption of DNA present in the sample is carried out during the course of incubation ranging from a few minutes to several hours, whatever the incubation temperature.

According to a preferred embodiment of the process conforming with the invention, the solid support is subjected to one or more washings after adsorption of DNA.

According to an advantageous modality of this mode of embodiment, the washing or washings of the solid support are carried out in 2.5 mM pH 8 trishydroxyaminomethane, 1 mM EDTA buffer.

According to another advantageous modality of this mode of embodiment, the washing or washings of the solid support are carried out in Borate buffer (ionic strength about 0.1), 0.1% Tween 20, (polyonethylene sorbitan monolaurate) pH 8–8.5.

According to a preferred mode of embodiment of the process conforming with the present invention, labelling of adsorbed DNA is carried out using a molecular biology reaction involving one or more enzymes specific to DNA, allowing incorporation of at least one deoxyribonucleotide triphosphate chemically labelled with a substance that can be detected at a later stage, for example, using an enzyme reaction.

According to an advantageous disposition of this mode of embodiment, labelling of DNA is carried out using a haplotomic cut displacement reaction ("Nick translation") by incorporation of at least one substance that can be detected at a later stage, for example, using an enzyme reaction.

According to an advantageous modality of this mode of embodiment, labelling during the course of the second step can be carried out during an incubation period ranging from a few minutes to several hours, in particular from 15 to 240 minutes (for example, 60 minutes) at a temperature ranging from about 15 to 40° Celsius (for example, 30° Celsius).

According to an advantageous disposition of this mode of embodiment, the nucleotide or nucleotides incorporated into the DNA are labelled with biotin and the enzyme used for its or their detection is related to avidin or streptavidin.

According to an advantageous disposition of this mode of embodiment of the process conforming with the invention, labelling by haplotomic cut displacement is carried out by incubation of DNA adsorbed onto the solid support with 10 to 100 picomoles of one or more label led deoxyribonucleotide triphosphates, possibly 10 to 100 picomoles of unlabelled deoxyribonucleotide triphosphates, about 0.04 units of DNA polymerase and about 4 picograms of deoxyribonuclease 1, in the presence of a buffer such as trishydroxyaminomethane (0.5–5 mM), magnesium chloride (2–5 mM) and possibly beta mercaptoethanol (7–15 mM), and bovine serum albumin (20–60 micrograms/ml).

According to a preferred mode of embodiment of the process conforming with the present invention, the solid support is subjected to one or more washings before detection of the marker quantitatively incorporated into DNA.

According to an advantageous modality of this mode of embodiment, any washing or washings are carried out in 0.2M Phosphate, 0.1M Citrate pH 5.4, 0.1% Tween 20 (polyoxyethylene sorbitan monolaurate) buffer.

According to another advantageous modality of this mode of embodiment, any washing or washings of the solid support are carried out in Borate buffer (ionic strength about 0.1), 0.1% Tween 20 (polyoxyethylene sorbitan monolaurate) pH 8–8.5.

According to a preferred mode of embodiment of the process conform with the present invention, detection of the marker incorporated into DNA is carried out by means of an enzymatic reaction using a substrate whose reaction in the presence of the corresponding enzyme emits a signal that can be quantified using a suitable apparatus.

According to an advantageous modality of this mode of embodiment, the marker incorporated into DNA being biotin, detection of this marker incorporated into DNA takes place by addition, during the course of a third step, of an avidin/enzyme or streptavidin/enzyme compound.

According to an advantageous modality of this mode of embodiment, the enzyme coupled to avidin or streptavidin is peroxidase.

According to an advantageous modality of this mode of embodiment, the streptavidin/peroxidase complex, previously diluted to a suitable concentration in 0.2M Phosphate, 0.1M Citrate pH 5.4, 4% polyethyleneglycol (6000) buffer is incubated for 5 to 30 minutes at a temperature of about 4 to 37° Celsius.

According to a preferred embodiment of the process conforming with the present invention, enzymatic activity of peroxidase is quantitatively determined after washing the solid support by addition of a substrate whose modification under the effect of the enzyme will give a measurable signal.

According to an advantageous modality of this mode of embodiment, any washing or washings are carried out in 0.2M Phosphate, 0.1M Citrate pH 5.4, 0.1% Tween 20 (polyoxyethylene sorbitan monolaurate) buffer.

According to another advantageous modality of this mode of embodiment, any washing or washings of the solid support are carried out in Borate buffer (ionic strength about 0.1), 0.1% Tween 20 (polyoxyethylene sorbitan monolaurate) , pH 8–8.5.

According to an advantageous modality of this mode of embodiment, enzymatic activity of peroxidase is determined quantitatively after washing the solid support in 0.2M Phosphate, 0.1M Citrate pH 5.4, 0.1% Tween 20 (polyoxyethylene sorbitan monolaurate) buffer by addition of 3, 3', 5 5'-tetramethylbenzidine. Reading the colored reaction is carried out a few minutes later, after stopping the reaction by addition of 2–4N sulfuric acid, on a spectrophotometer at 450 nm.

In addition to the preceding dispositions, the invention further includes other dispositions which will become apparent from the following description.

The present invention is more particularly aimed at (i) the new process for dosing DNA present in biological liquid in an extracellular position, conforming with the preceding dispositions, (ii) biological analyses using this process, as well as (iii) elucidated physiological and pathological situations and (iv) diagnoses established by means of the process of with the present invention.

The invention will be better understood from the following examples describing the embodiment and application of the process which is the subject of the present invention. However, it should be understood that these examples are given solely for purposes of illustration and do not limit the invention in any way whatsoever.

EXAMPLE 1 detection of DNA circulating in the plasma sensitization of the microtitration plate: 50 µl of histonic proteins at 10 µg/ml in 0.1M carbonate buffer pH 9.6. Incubation for 24 hours at 4° C. followed by three washings in Borate buffer (ionic strength 0.1) 0.1% Tween 20 (polyoxyethlene sorbitan monolaurate).

adsorption of DNA onto the solid support: incubation of 50 µl of plasma for 15 minutes at 30° C.

labelling of DNA after 3 washings in 2.5 mM trishydroxyaminomethane buffer pH 8,1 mM EDTA (ethylenediamine tetra-acetic acid), addition of 50 µl of reaction medium 0.5 mM Trishydroxyaminomethane 0.1M pH 8,3 mM $MgCl_2$, 50 pg/ml BSA, 9 mM beta 2 mercaptoethanol and containing 40 picomoles of biotin 14-dATP, 20 picomoles of dGTP, dTTP and dCTP, 0.04 units of DNA polymerase and 4 picograms of pancreatic deoxyribonuclease I and incubation for 1 hour at 30° C.

detection of labelling after three washings in 0.2M Phosphate/0.1M Citrate pH 5.4 0.1% Tween 20 (polyoxyethylene sorbitan monolaurate) buffer, addition of 40 μl of streptavidin/peroxidase conjugate (Amersham) diluted to 1/1000 in Phosphate/Citrate 4% polyethyleneglycol buffer. After 15 minutes of incubation at 30° C. and four washings in 0.2M Phosphate/ 0.1M Citrate pH 5.4, 0.1% Tween 20 (polyoxyethylene sorbitan monolaurate) buffer, addition of 50 μl of substrate (3, 3' 5 5' tetramethyl-benzidine). After a few minutes, the coloured reaction is stopped by addition of 50 μl of 4N $H_2SO_4$ and reading is carried out at 450 nm on a "Multiscan Flow" spectrophotometer.

EXAMPLE 2 detection of DNA circulating in the plasma of a mouse injected with bacterial endotoxin (or lipopolysaccharide: LPS) and in the plasma of a normal mouse, using a microtitration plate sensitized by histonic proteins as a solid support (Table I).

sensitization of the microtitration plate: 50 μl of histonic proteins at 10 μg/ml in 0.1M carbonate buffer pH 9.6. Incubation for 24 hours at 4° C. followed by three washings in Borate buffer (ionic strength 0.1) 0.1% Tween 20 (polyoxyethlene sorbitan monolaurate) pH 8.3.

adsorption of DNA onto the solid support: incubation of 35 μl of mouse plasma at different dilutions for 120 minutes at 30° C.

labelling of DNA after 3 washings in 2.5 mM trishydroxyaminomethane buffer pH 8, 1 mM EDTA (ethylene diamine tetra-acetic acid), addition of 35 μl of reaction medium 0.5 mM Trishydroxyaminomethane 0.1M pH 8, 3 mM $MgCl_2$, 50 μg/ml BSA, 9 mM beta 2 mercaptoethanol and containing 40 picomoles of biotin 14-dATP, 20 picomoles of dGTP, dTTP and dCTP, 0.04 units of DNA polymerase and 4 picograms of pancreatic deoxyribonuclease I and incubation for 2 hours at 30° C.

detection of labelling after three washings in 0.2M Phosphate/0.1M Citrate pH 5.4, 0.1% Tween 20 (polyoxyethylene sorbitan monolaurate) buffer, addition of 40 μl of streptavidin/peroxidase conjugate (BRL) diluted to 1/1000 in Phosphate/Citrate 4% polyethyleneglycol buffer. After 30 minutes of incubation at 30° C. and four washings in 0.2M Phosphate/0.1M Citrate pH 5.4, 0.1% Tween 20 (polyoxyethylene sorbitan monolaurate) buffer, addition of 50 μl of substrate (3 3' 5' tetramethylbenzidine). After a few minutes, the coloured reaction is stopped by addition of 50 μl of 4N $H_2SO_4$ and reading is carried out at 450 nm on a "Multiscan Flow" spectrophotometer.

TABLE I

Detection of circulating DNA in the plasma of a mouse injected with LPS and in the plasma of a normal mouse

|  | dilution | OD[1] Units (OD x 1000) | |
|---|---|---|---|
|  |  | wells sensitized by histones | non-sensitized wells |
| "LPS" plasma[2] | 1/3 | 1462 | 128 |
|  | 1/15 | 972 | 90 |

TABLE I-continued

Detection of circulating DNA in the plasma of a mouse injected with LPS and in the plasma of a normal mouse

|  | dilution | OD[1] Units (OD x 1000) | |
|---|---|---|---|
|  |  | wells sensitized by histones | non-sensitized wells |
| normal plasma[3] | 1/3 | 116 | 122 |
|  | 1/15 | 101 | 103 |

[1]: OD = optical density
[2]: female mouse plasma OF1 aged eight weeks injected eight hours before bleeding by intraperitoneal route with 100 micrograms of LPS from Salmonella minnesota Re 595 diluted in 0.15 M NaCl (0.2 ml).
[3]: female mouse OF1 aged eight weeks injected eight hours before bleeding with 0.2 ml of 0.15 M NaCl.

EXAMPLE 3 detection of DNA circulating in the plasma of a mouse injected with bacterial endotoxin dosed at different dilutions in the plasma of a normal mouse, using a microtitration plate sensitized by histonic proteins as a solid support (Table II).

The methodology is identical to that described in example 2. The results obtained have been corrected for the OD value obtained from the plasma of the normal mouse.

TABLE II

Effect of dilutions

| Dilution[1] | OD[2] |
|---|---|
| 1/5.6 | 1412 |
| 1/22 | 1063 |
| 1/90 | 523 |
| 1/360 | 192 |
| 1/1400 | 76 |
| 1/5700 | 26 |

[1]: dilution of the plasma of a mouse injected with bacterial endotoxin (LPS) in the plasma of a normal mouse (NMP).
[2]: OD:optical density. The results are expressed by the difference in OD units (OD x 1000) between the value given by the plasma of a mouse injected with LPS diluted in NMP and that given by NMP.

EXAMPLE 4 dosage of DNA of different origin. (Table III).

The methodoloy used to dose identical amounts of DNA of different origin is identical to that used in examples 2 and 3.

Dosages were carried out on 35 μl of DNA at 731 ng/ml of 4 different origins:

TABLE III

Dosage of DNA of different origin

| DNA[1] | OD units |
|---|---|
| A | 1127 |
| B | 1007 |
| C | 991 |

TABLE III-continued

Dosage of DNA of different origin

| DNA[1] | OD units |
|--------|----------|
| D      | 1195     |
| /[2]   | 182      |

[1]: Origin of dosed DNA:
A: bacteriophage (MP2, Boerhinger Mannheim)
B: plasmid (PBR 322, Boerhinger Mannheim)
C: calf thymus (V Sigma type)
D: mononucleosome extracted from hamster cells CHO
[2]: /= negative control (0.15 M NaCl)

EXAMPLE 5 dosage of DNA in the plasma of a mouse injected with LPS diluted to ¼ in normal mouse plasma (NMP). Effect of the length of adsorption and labelling steps. Control of the specificity of the dosage (Table IV).

The methodology used is described in example 1. Two adsorption times (15 and 60 minutes) and four labelling times (15, 30, 60, 120 minutes) were tested. The specificity of the dosage was controlled by omitting enzymes specific to DNA in the reaction medium for labelling DNA.

TABLE IV

Effect of the length of the adsorption and labelling steps and control of the specificity of dosage

| duration of the step (minutes) | | OD units (OD × 1000) | | | |
|---|---|---|---|---|---|
| | | plasma of mouse injected with LPS | | NMP | |
| adsorption | labelling | +[1] | −[2] | + | − |
| 15 | 15  | 938  | 188 | 232 | 199 |
| 15 | 30  | 1141 | 212 | 242 | 214 |
| 15 | 60  | 1453 | 219 | 246 | 203 |
| 15 | 120 | 1478 | 224 | 262 | 212 |
| 60 | 15  | 961  | 114 | 160 | 122 |
| 60 | 30  | 1064 | 116 | 149 | 111 |
| 60 | 60  | 1387 | 107 | 162 | 99  |
| 60 | 120 | 1444 | 190 | 276 | 180 |

[1]: +:enzymes specific to DNA present.
[2]: (−):enzymes specific to DNA absent.

From the preceding examples of application, it emerges that the process which is the subject of the present invention allows DNA to be quantitatively dosed in the plasma and, in general, in a biological medium containing on the order of 1000 times more proteins than DNA and constitutes a process which is easy to set up, requiring only an apparatus to read optical density in the visible spectrum. The process conform with the present invention is reproducible and sufficiently sensitive to detect DNA in samples of only a few microliters at concentrations in the order of nanograms per milliliter.

Moreover, the process conform with the present invention is faster and allows simultaneous dosage of at least 10 times more samples than the processes of the prior art.

The process conform with the present invention should, because of the advantages it presents as described in the preceding pages, allow a better understanding of the physiological and physiopathological significance of an increase in plasma DNA levels in man, as well as under experimental conditions, and should constitute a highly valuable tool for the study of all situations where it is important to quantify cell death phenomena or to detect contamination of biological samples by DNA.

As emerges from the preceding description, the invention is in no way limited to the modes of embodiment and application described in detail above. To the contrary, it embraces any variations which might occur to any person skilled in the art without diverging from the context or scope of the present invention.

What is claimed is:

1. A process for quantifying DNA present in an extracellular position in a sample medium, which comprises the following steps:
   fixation of DNA present in the medium by adsorption onto a solid support;
   incorporation into said fixed DNA of at least one labelled deoxyribonucleotide as a marker to label said fixed DNA; and
   direct or indirect detection of the incorporated marker on said fixed DNA.

2. A process according to claim 1 wherein said solid support is a microtitration plate or a membrane.

3. A process according to claim 1 wherein the substance having an affinity for DNA for fixing said DNA indirectly binds DNA to said solid support.

4. A process according to claim 1 wherein said fixation of DNA is carried out by adsorption using a substance having an affinity for DNA sufficient to directly bind DNA to said support.

5. A process according to claim 4 wherein the substance having an affinity for DNA, by means of which DNA fixation onto the support is carried out, are cationic substances.

6. A process according to claim 5 wherein the substance having an affinity for DNA, by means of which DNA fixation on the support is carried out, is one or more histones.

7. A process according to claim 6 wherein fixation of DNA onto the support is carried out after sensitization of the solid support by incubation in a mixture of histonic proteins in 0.0514 0.1M carbonate buffer pH about 9.6, for several hours.

8. A process according to claim 3 wherein adsorption of DNA present in the medium is carried out during the course of incubation for a period of 15 to 20 minutes.

9. A process according to claim 8 wherein the solid support is subjected to one or more washings before labelling of adsorbed DNA is carried out.

10. A process according to claim 9 wherein the solid support is subjected to one or more washings in 2.5 mM Tris pH 8, mM EDTA buffer before labelling of adsorbed DNA is carried out.

11. A process according to claim 10 wherein labelling of adsorbed DNA is carried out using enzymes specific to DNA.

12. A process according to claim 11 wherein labelling of DNA is carried out using a haplotomic cut displacement reaction ("Nick translation") or using any other DNA-labelling technique during the course of incubation for 15 to 240 minutes, at a temperature ranging from about 15 to 40° C.

13. A process according to claim 12 wherein labelling of DNA is by "primer labelling" or "terminal labelling".

14. A process according to claim 12 wherein the nucleotide or nucleotides incorporated into the DNA are labelled with biotin and the enzyme used for its or their detection is coupled to avidin or streptavidin.

15. A process according to claim 14 wherein labelling by haplotomic cut displacement is carried out by incubation of DNA adsorbed onto the solid support with about 10 to 100 picomoles of one or more labelled deoxyribonucleotide triphosphates, about 10 to 100 picomoles of one or more unlabelled deoxyribonucleotide triphosphates, about 0.04 units of DNA polymerase and about 4 picograms of deoxyribonuclease I, in the presence of a buffer.

16. A process according to claim 15 wherein said buffer is trishydroxyaminomethane (0.5–5 mM), magnesium chloride (2–5 mM) and beta mercaptoethanol (7–15 mM), or bovine serum albumin (20–60 micrograms/ml).

17. A process according to claim 15 wherein, after labelling DNA, the solid support is subjected to one or more washings before detection of the marker quantitatively incorporated into DNA is carried out.

18. A process according to claim 17 wherein, after labelling DNA, washings are carried out in 0.2M Phosphate, 0.1M Citrate pH 5.4, 0.1% Tween 20 buffer.

19. A process according to claim 18 wherein detection of the marker incorporated into DNA is carried out by means of an enzymatic reaction.

20. A process according to claim 19 wherein the marker incorporated is biotin and detection of this marker incorporated into DNA is carried out by addition of an avidin/enzyme or streptavidin/enzyme compound, known as the conjugate.

21. A process according to claim 20 wherein the enzyme coupled to avidin or streptavidin is peroxidase.

22. A process according to claim 21 wherein the peroxidase coupled to avidin or streptavidin is in 0.2M Phosphate, 0.1M Citrate pH 5.4, 4% polyethylene glycol (6000) buffer.

23. A process according to claim 22 wherein the peroxidase coupled to avidin or streptavidin is incubated for five to 30 minutes at a temperature of about 4 to 37° C. in the presence of DNA labelled with biotin.

24. A process according to claim 23 wherein, after incubation of the conjugate, the solid support is subjected to one or more washings.

25. A process according to claim 24 wherein the washing or washings are carried out in Borate (ionic strength about 0.1), 0.1% Tween 20, pH 8.3 buffer.

26. A process according to claim 24 wherein, after incubation of the conjugate, washing or washings of the solid support is carried out in 0.2M Phosphate, 0.1 M Citrate pH 5.4, 0.1% Tween 20 buffer.

27. A process according to claim 26 wherein the presence of the conjugate is detected using any substrate whose reaction in the presence of the conjugate leads to a quantifiable signal on a spectrophotometer, spectrofluorimeter or biosensor.

28. A process according to claim 27 wherein the enzymatic activity of peroxidase is quantitatively determined by addition of 3,3', 5,5'-tetramethylbenzidine which produces a colored reaction which causes a colored product.

29. A process according to claim 28 wherein said colored product is read on a spectrophotometer at 450 nm after stopping the reaction by the addition of 2–4N sulfuric acid.

* * * * *